US007008797B2

(12) United States Patent
Alexandridis et al.

(10) Patent No.: US 7,008,797 B2
(45) Date of Patent: *Mar. 7, 2006

(54) RECOVERY OF LIQUIDS FROM ABSORBENT PACKAGING MATERIALS

(75) Inventors: Paschalis Alexandridis, Amherst, NY (US); Sriram Neelamegham, Amherst, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 97 days.

This patent is subject to a terminal disclaimer.

(21) Appl. No.: 10/615,056

(22) Filed: Jul. 8, 2003

(65) Prior Publication Data

US 2004/0108269 A1 Jun. 10, 2004

Related U.S. Application Data

(63) Continuation-in-part of application No. 09/866,169, filed on May 25, 2001, now Pat. No. 6,589,797.

(60) Provisional application No. 60/226,406, filed on Aug. 18, 2000, provisional application No. 60/207,612, filed on May 26, 2000.

(51) Int. Cl.
*G01N 1/00* (2006.01)

(52) U.S. Cl. .................. 436/176; 436/177; 436/178; 210/634

(58) Field of Classification Search ............... 210/634, 210/643, 644, 645, 650, 651; 422/56, 58, 422/61, 102; 436/165, 169, 174–178; 206/204, 206/484, 524.7; 383/109, 113

See application file for complete search history.

(56) References Cited

U.S. PATENT DOCUMENTS

| 5,075,221 A | * | 12/1991 | Mauck et al. ............... 435/7.36 |
| 5,124,041 A | | 6/1992 | Sheer et al. |
| 5,525,475 A | | 6/1996 | Ladouceur |
| 5,770,086 A | | 6/1998 | Indriksons et al. |
| 5,984,087 A | | 11/1999 | Hacikyan |
| 6,161,687 A | | 12/2000 | Hacikyan |
| 6,308,827 B1 | | 10/2001 | Hacikyan |
| 6,523,681 B1 | * | 2/2003 | Hacikyan .................... 206/204 |

OTHER PUBLICATIONS

Robert H. Perry et al., Perry's Chemical Engineering Handbook, 6th Ed., 1984, pp. 3-97 to 3-100.

* cited by examiner

*Primary Examiner*—Joseph Drodge

(57) ABSTRACT

The present invention describes a method for recovery of aqueous samples or components thereof from polymer packaging materials, wherein the spilled aqueous sample has been absorbed by the packaging material to form a liquid swollen absorbent gel. The method comprises the steps of contacting the liquid swollen absorbent gel with a recovery fluid, wherein the recovery fluid has a higher osmotic pressure than the aqueous sample.

23 Claims, 4 Drawing Sheets

1

RECOVERY OF LIQUIDS FROM ABSORBENT PACKAGING MATERIALS

This application is a continuation-in-part of U.S. Nonprovisional application Ser. No. 09/866,169 filed May 25, 2001 (now U.S. Pat. No. 6,589,797, which in turn claims priority to U.S. Provisional Application Ser. No. 60/207,612, filed May 26, 2000, and U.S. Provisional Application Ser. No. 60/226,406, filed Aug. 18, 2000, the disclosures of which are incorporated herein by reference.

FIELD OF THE INVENTION

This invention relates generally to the field of polymer packaging materials for aqueous samples. More particularly, this invention provides a novel method for the recovery of spilled aqueous samples or components thereof from polymer packaging materials.

BACKGROUND OF THE INVENTION

Several packaging materials have been designed and applied for the transportation and disposal or analysis of aqueous samples including body fluids such as urine, plasma and blood. These packages can be of various shapes, sizes and forms, such as cylindrical, spherical, pouch-like or carton-like, and typically consist of a sealable, multi-layered container with a central layer consisting of cross-linked ionized and/or ionizable polymers. Examples of such polymers include sodium polyacrylate based formulations like $(C_3H_3O_2Na)_n$ and variations thereof such as those described in U.S. Pat. Nos. 6,161,687 and 5,984,087. Surrounding the central layer is: (i) an outer layer made of a material which is non-permeable to liquids, including certain types of paper, cardboard, wood or polymer laminate based on thermoplastic resins, vinyl polymers, polyolefins or polyesters, and (ii) an inner layer made of water permeable or water-soluble compounds such as starch paper, cellulose-based films or other water-soluble synthetic films.

When a liquid enclosed within such a multi-layered package leaks inside the container, it passes through the inner water-soluble layer and is absorbed by the absorbent material (the cross-linked polymer). This results in the formation of a liquid-swollen absorbent gel. The ability of the absorbent material to swell with the liquid and to form a gel has applications including, but not limited to, the containment and immobilization of a liquid spill. When the fluid sample in the gel is unique or precious, as may happen during the transport and testing of blood or DNA samples required for criminal investigations, DWI cases, drug abuse tests related to athletic events, regular workplace check-ups and the like, the containment alone of spilled samples is insufficient. In such cases, the recovery of the sample fluid and its subsequent testing is critical.

Thus, in the field of packaging materials, there is a need for a methodology to recover liquids such as biological samples spilled into the packaging materials.

SUMMARY OF THE INVENTION

Figure 1A:
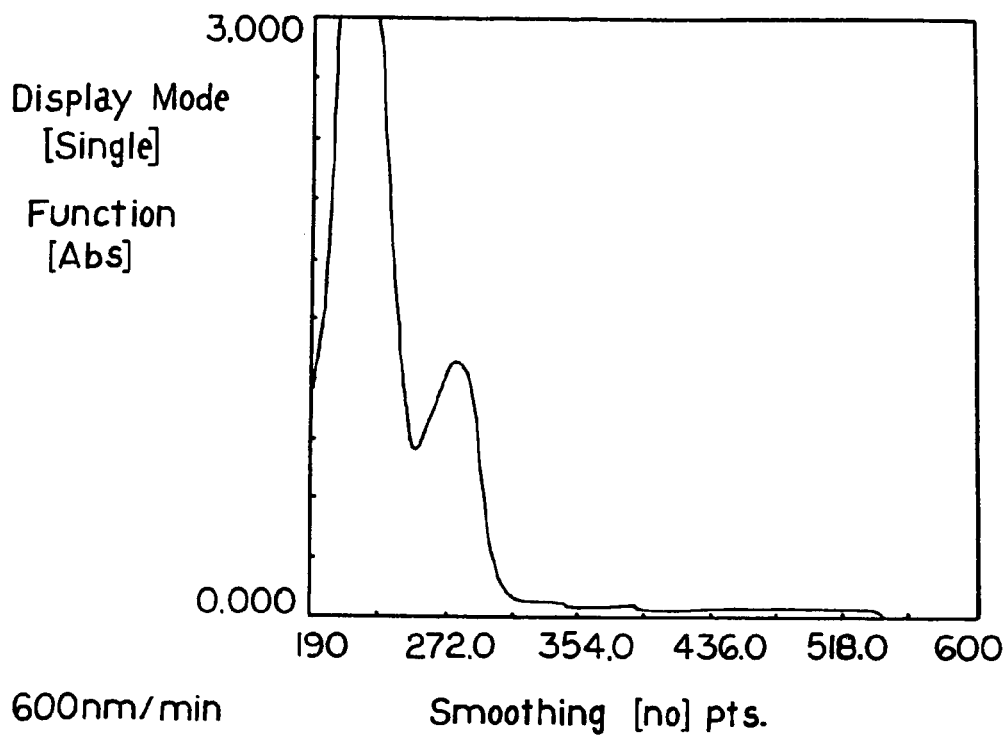
FIGS. 1A–1C are representations of UV/Visible scan of 1:20 (i.e. concentration is 0.05×) dilution of human blood plasma (FIG. 1A), 2.75 mg/ml SA60S polymer alone in aqueous solution (FIG. 1B), and 1:20 dilution (or 0.05×) plasma containing 2.75 mg/ml SA60S (FIG. 1C).

The present invention discloses compositions and methods for recovering aqueous samples from polymer packaging materials such that quantitation of desired analytes in the recovered samples can be carried out. The sample may be biological or non-biological aqueous samples or components thereof. The method comprises the steps of contacting the packaging material which has absorbed the aqueous sample and formed a liquid-swollen absorbent gel with a recovery fluid, disrupting the liquid-swollen absorbent gel, and recovering the aqueous sample for analysis of desired analytes.

Accordingly, an object of the present invention is to provide a recovery fluid for recovery of the aqueous samples or components thereof from polymer packaging materials.

Another object of the present invention is to provide a method for the recovery of aqueous samples or components thereof from polymer packaging materials.

DETAILED DESCRIPTION OF THE INVENTION

The term "aqueous" as used herein, means any fluid having $H_2O$ at greater than 20% of its volume. Aqueous samples may be biological samples or non-biological samples.

The term "biological samples" as used herein, means any sample obtained from living materials, or containing cells, progeny thereof, or extracts and components thereof. Thus, biological samples include, but are not limited to, any body fluid such as blood, plasma, lymph, urine, cerebrospinal fluid, amniotic fluid and the like, and tissue culture materials such as supernatants, cell homogenates and the like. Biological samples may contain non-physiological substances such as toxic and non-toxic chemicals, pharmacological drugs and alcohol.

The term "non-biological" fluids or samples refers to any aqueous solution that is not directly obtained from living materials. Thus non-biological samples include, but are not limited to, water or water based solutions from industry, or contaminated aqueous samples from streams, rivers or other water bodies. Non-biological fluids may contain biological materials including, but not limited to, microbes or components thereof.

The term "liquid-swollen absorbent gel" as used herein means, any polymer gel packaging material which has absorbed an aqueous sample such as a biological or non-biological sample.

The term "recovery fluid" as used herein means a fluid having a higher osmolarity than the aqueous sample. This recovery fluid is contacted with the liquid-swollen absorbent gel to recover the aqueous sample or components thereof.

This invention describes compositions and methods for recovering spilled aqueous samples from absorbent packaging materials. The packaging materials, upon coming in contact with the aqueous samples form liquid-swollen absorbent gels. The method of the present invention comprises the steps of contacting the liquid swollen absorbent gel with a recovery fluid, disrupting the gel and recovering the aqueous sample for detection/analysis of desired analytes.

The recovery fluid of the present invention comprises a fluid that can penetrate the liquid-swollen absorbent gel. The recovery fluid should have an osmotic pressure that is higher than the aqueous sample to be recovered. It is expected that the osmotic pressure of the liquid swollen absorbent gel will be similar to that of the aqueous sample. Thus, the recovery fluid should have an osmotic pressure higher than that prevailing in the liquid-swollen absorbent gel. A suitable recovery fluid will have as osmotic pressure in the range of 1–150 atm. It is preferable to use a recovery fluid that has an osmotic pressure which is about 5 times higher than that prevailing in the liquid-swollen absorbent gel or of the aqueous sample. Such recovery fluids can be generated by the addition of water to water-soluble species. In one embodiment, ionic (charged) species, preferably inorganic charged species, such as sodium chloride (NaCl) are used. Other salts that contain univalent, divalent and larger valency metal ions can also be used. To achieve high osmotic pressure, salts with high molar solubility (i.e., measured in units of moles per volume) and valency are preferable. Examples of such highly soluble compounds are provided here along with their solubility in grams per 100 cc solution at 20° C.: $NH_4NO_3$ (192 g/100 cc solution), $KC_2H_3O_2$ (255 g/100 cc solution), $KNO_2$ (298 g/100 cc solution), KCNS (217 g/100 cc solution), NaCl (36 g/100 cc solution). Examples of other similar molecules are listed in Table 3.120 in Perry's Chemical Engineering Handbool, $6^{th}$ ed., 1984, pp 3-97 to 3-100, which table is incorporated herein by reference. In cases where the recovery fluid is composed of monovalent ionic species (e.g., NaCl or $NH_4NO_3$), additional components such as those that chelate divalent ions (e.g., EDTA, citrate) may also be added. In another embodiment, simple carbohydrate molecules such as glucose, fructose, sucrose and the like can also be used. Those skilled in the art will recognize that many other small water soluble molecule can be used in the recovery fluid. It is preferable to use molecules that have a molecular weight less than 1000 Da. Additional substances added to the fluid may include preservatives such as azides, bactericides, and colored compounds for easy visual detection. It will be recognized by those skilled in the art that minor variations in the composition of the recovery fluid may be required so that the components in the fluid are not the same as the analyte. Also the composition of the recovery fluid may be changed such that it does not interfere with the recovery or analysis of the analyte. For example, if glucose is being detected as the analyte, glucose should not be used in the recovery fluid. Also, if the detection protocol involves the use of immunoassays or diagnostic kits where high concentrations of NaCl interfere with the detection, this salt may be replaced with other ionic species, as listed above.

The recovery fluid of the present invention is suitable for use with any polymer packaging material (such as sodium acrylate) that absorbs liquids on the basis of osmotic pressure difference between the polymer interior and the surrounding liquid. The polymer of the packaging material may be cross linked. Examples of packaging materials may be found in U.S. Pat. Nos. 5,984,081 and 6,161,687. Several packaging materials are commercially available. These include, but are not limited to, SA60S (Gelok Innternational Corp., Dunbridge, Ohio), Aridall 1460 and 2260(Chemical Corp., Stokie, Ill.), AQUA KEEP® J-550 (Sumitomo Seika Chemical Co., Osaka, Japan; Absorbent Technologies, Muscatine, Iowa), FLOSORB 60® (SNF-Floerger, Cedex, France) and WATER LOCK J-550 (Grain Processing Corp.). The polymer packaging materials also include those which comprise absorbent fibers, absorbent granules or combinations thereof. These are typically composite materials woven inside a laminate material. The absorbent fibers may be superabsorbent fibers. Examples of absorbent fibers are Latex Bonded Airlaid supply with mono-component or bi-component fibers or superabsorbent fibers, Thermal Bonded Airlaid supply with mono-component or bi-component fibers or superabsorbent fibers, and Thermal-Latex Bonded Airlaid supply with mono-component or bi-component fibers or superabsorbent fibers (Concert GMBH, Germany). The absorbent granules may be superabsorbent granules.

Preferably just as the components of the recovery fluid and the desired analyte should be mutually excluded for successful detection, similarly, the components of packaging polymer and the analyte may also be adjusted so that there is no match between the two. Also components of the polymer may be adjusted so that it itself does not interfere with the assay. Thus, there will be no interference with detection and quantification of the test sample. As an example, if sodium in the sodium acrylate interferes with the immunoassay or is the analyte being detected, potassium acrylate polymers may instead be used as the packaging material.

The recovery fluid can be stored at 4° C. If some of the salts precipitate during storage, these can be re-dissolved by warming to room temperature or to a higher temperature prior to usage. It is preferable not to freeze the recovery fluid during storage.

Upon leakage of aqueous liquids that are packaged in the polymer packaging materials, a gel forms and is referred to herein as liquid-swollen absorbent gel. It is expected that the user knows the approximate amount of biological fluid that has leaked, and wetted the packaging material. In cases where a known amount of fluid is stored in a vial and all of it has leaked, this equals the amount of fluid in the vial. In other instances, where only part of the fluid has leaked into the absorbent packaging, appropriate weighing or volumetric measurement techniques can be used to determine the amount of fluid that has been absorbed by the packaging. Typically, it is expected that the weight of the liquid-absorbed polymer is primarily due to the weight of the leaked liquid since the polymer weight is negligible. Hence, even if the quantity of the leaked liquid is not precisely known, this can be determined by placing a certain amount of the liquid-swollen polymer on a standard weighing instrument and measuring its mass. The volume of liquid in this unknown amount of liquid-swollen gel can then be determined by taking the product of mass times the liquid density: for aqueous solutions the density is typically ~1 g/cc. Alternatively, other standard instruments can also be used to measure the volume of a given amount of the liquid swollen absorbent gel without an intermediate weighing step.

In a preferred embodiment, approximately 5 times the amount of the recovery fluid as the amount of fluid that has leaked can be added to the liquid-swollen gel. The dilution factor for blood in this case is 5 and the extent of dilution is 6 fold.

The nature of recovery fluid application to the sample preparation depends on whether the sample being tested is volatile (e.g. blood alcohol) or not (e.g. protein/drug/hormone levels in blood) as detailed herein. Further, if by simple visual inspection, it is evident that only a part of the absorbent polymer has been wetted by the leaked fluid the recovery fluid may be applied to only the wetted part of the packaging while discarding the remainder.

In cases where the container containing the liquid-swollen absorbent gel is sealed, as is typically the case when one or more of the fluid components is volatile (e.g., for detection of alcohol in blood), the recovery fluid can be applied to the contents by injecting the fluid into the container by suitable means such as with the help of a syringe. For volatile products it is preferable that the sample be not exposed to excess air. The perforation is therefore sealed after removal of the syringe.

In cases where the container containing the liquid-swollen absorbent gel is open or where the container containing the liquid-swollen absorbent gel is sealed but none of the components are volatile, the container may be perforated. This may be achieved by either cutting a piece of the container or cutting open the entire container. The weight/volume of the leaked sample in the pouch/container may be known or may be determined using a combination of weighing and volumetric measurement methods as described above. Further, the area of the container piece containing the liquid-swollen absorbent gel can be measured to get an estimate of the amount of polymer used in the absorption process. The amount of the high-osmolarity recovery fluid added to the liquid-swollen absorbent gel should generally be more than the amount of liquid sample in the absorbent gel, preferably 1–5 times more.

The recovery fluid is allowed to contact the liquid-swollen absorbent gel for a suitable period of time. For example, an incubation time of about 5 to 10 minutes can be used. Mixing or shaking the liquid-swollen absorbent gel with the recovery fluid will facilitate the penetration of the recovery fluid into the gel. The addition of the recovery fluid results in disruption of the gel. To establish that the gel has been disrupted, the mixture may be checked visually, by touch or by stirring. Free-flowing liquid having a consistency such that it does not markedly resist flow indicates that the gel has been disrupted. Some small pieces of gel may be observed in the recovery fluid. If the gel is not sufficiently disrupted, additional incubation may be carried out and/or more high-osmolarity recovery fluid may be added.

Following disruption of the gel, an aliquot can be removed for analysis. In the case where the gel is in a sealed container, a syringe may be used to remove an aliquot of the sample. In the case, where the container has been opened, or where the container has been cut and the desired portion of the container has been placed in contact with the recovery fluid, an aliquot of the resulting mixture can be removed for analysis using a pipette or by weight measurement.

It should be noted that none of the components of the recovery fluid are themselves hazardous. However, addition of the recovery fluid to the sample does not make the biological specimen non-hazardous. Thus, standard OSHA protocols should be followed while handing hazardous material alone, or when handling the recovery fluid after it has come in contact with the hazardous material.

The recovered materials can be used for the detection, quantitation or analysis of desired analytes. In general, a majority of clinical tests used in diagnostics and immunoassays are color-based i.e. they observe changes in analyte concentration based on magnitude of light absorbed or magnitude of light emitted (fluorescence). In this regard, the negligible absorbance/fluorescence of acrylic acid based polymers (like SA60S which do not contain ringed and double/triple bonded chemical structures) makes them ideally suited for use as absorbent polymer packaging materials.

For the purposes of illustration the following examples are presented below.

EXAMPLE 1

Figure 1B:
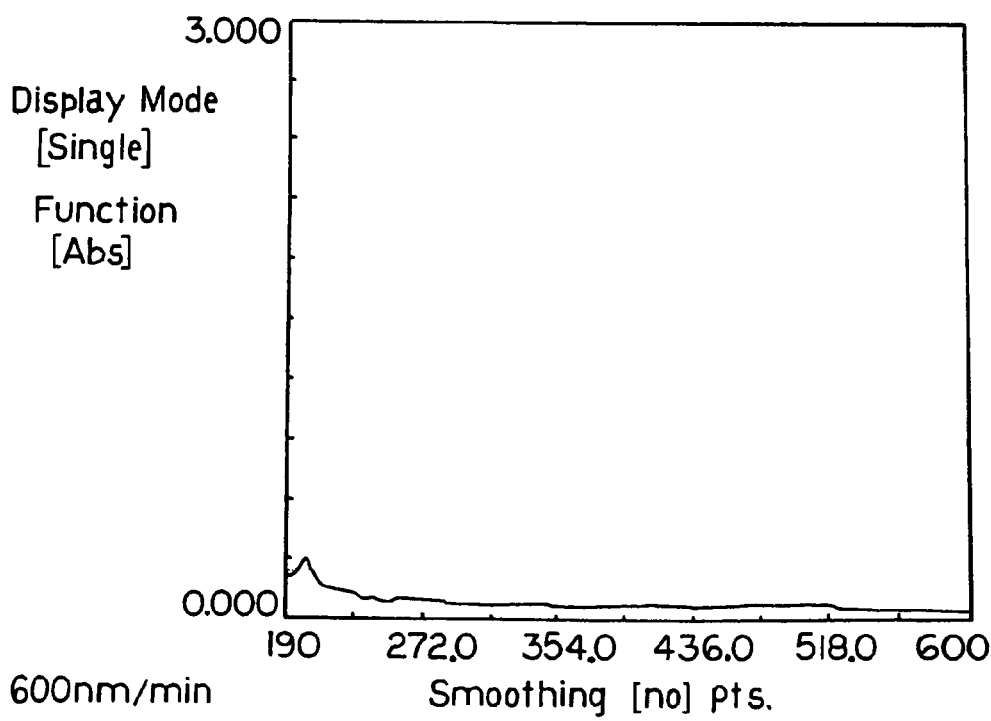
Figure 1C:
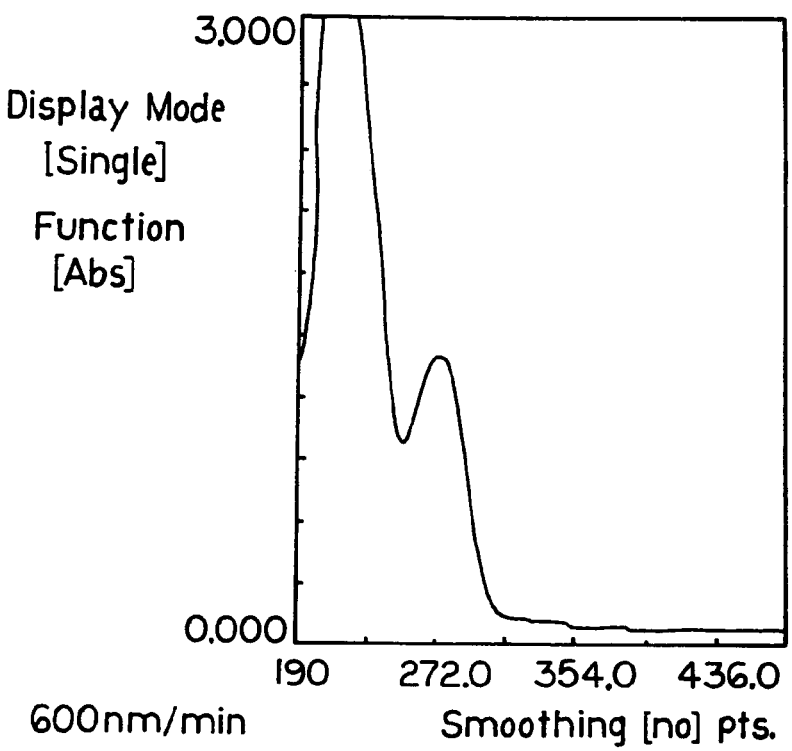
Figure 2:
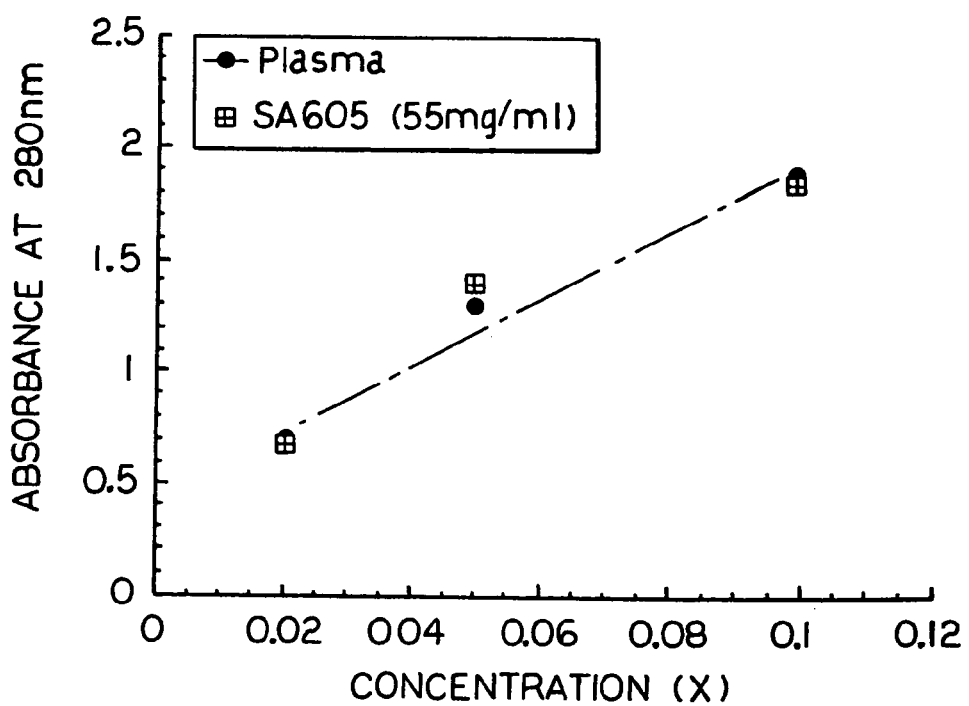
FIG. 2 is a representation of the relationship between absorbance and concentration of total protein in plasma alone, and in plasma containing SA60S.

This embodiment demonstrates that detection of analytes in plasma is not affected by the presence of the absorbent packaging polymers. To illustrate this embodiment, the protein content in human blood plasma was analyzed in the presence or absence of absorbent polymers. Venous blood was collected from healthy individuals and suspended in 10% w/v sodium citrate solution. Platelet poor plasma (PPP) was isolated by centrifugation at 2500 rpm for approximately 15 minutes. The isolated plasma is assumed to have an initial concentration of 1×. The concentration dependent absorbance profile of plasma in phosphate buffered saline (PBS) (0.144 g/L $KH_2PO_4$, 9.0 g/L NaCl, 0.795 g/L $Na_2HPO_4.7H_2O$) was obtained at a wavelength of 280 nm. Then 55 mg/ml of polymer SA60S (Absorbent Technologies, Dunbridge, Ohio) was dissolved in 1 ml of plasma solution (initial plasma concentration of 1×), and diluted in PBS to concentrations ranging from 0.02–0.1×. SA60S is a commercially available poly(acrylic acid) and poly(sodium acrylate) mixed polymer which is mildly surface crosslinked. Upon dilution with PBS in these experiments, the SA60S concentration varied from 0.11 to 5.5 mg/ml. The absorbance intensity of samples was then measured at 280 nm for detection of total protein content in the polymer-plasma solution. UV/Visible scans of 0.05× plasma alone, SA60S alone and 2.75 mg/ml SA60S in 0.05× plasma are shown in FIGS. 1A, 1B and 1C respectively. As seen, SA60S does not absorb light in the UV/visible range or alter the absorbance properties of proteins in plasma. A linear relationship between the concentration of plasma and total protein content was observed for plasma alone as well as for plasma in the presence of SA60S. These experiments demonstrate that polymer SA60S does not interfere with the detection of proteins in aqueous solutions.

EXAMPLE 2

Figure 3:
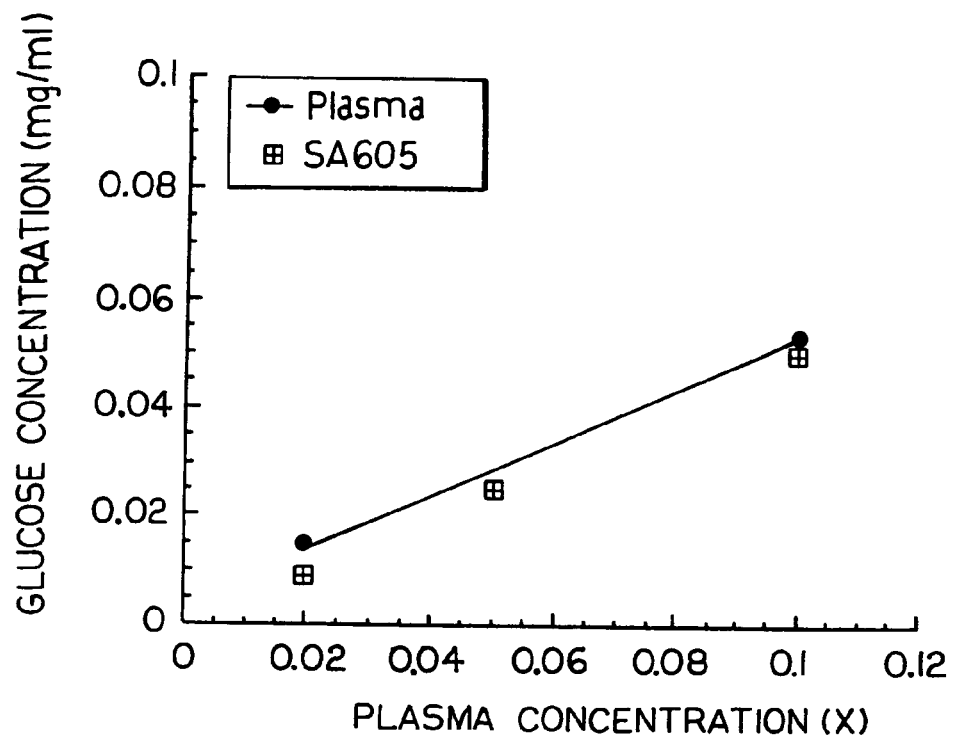
FIG. 3 is a representation of the relationship between glucose concentration (mg/ml) and plasma concentration measured in plasma alone or in plasma containing SA60S polymer.

In another illustration, glucose concentration was measured in the presence or absence of absorbent polymer packaging materials to demonstrate that absorbent polymers do not affect the measurement. In these experiments, 50 µl of a glucose-containing solution and 100 µl of assay reagent from a glucose assay kit (SIGMA Chemical Co.) were added to a multi-well plate and incubated at 37° C. for 30 minutes. The reaction was quenched with 20 µl of concentrated sulphuric acid and absorbance was measured at 540 nm. FIG. 3 is a comparison of the correlation between glucose concentration and plasma concentration for plasma alone, and plasma containing SA60S at dilutions ranging from 0.1 to 0.02×. These data indicate that detection of glucose is not affected by the presence of the polymer SA60S in plasma.

EXAMPLE 3

Figure 4:
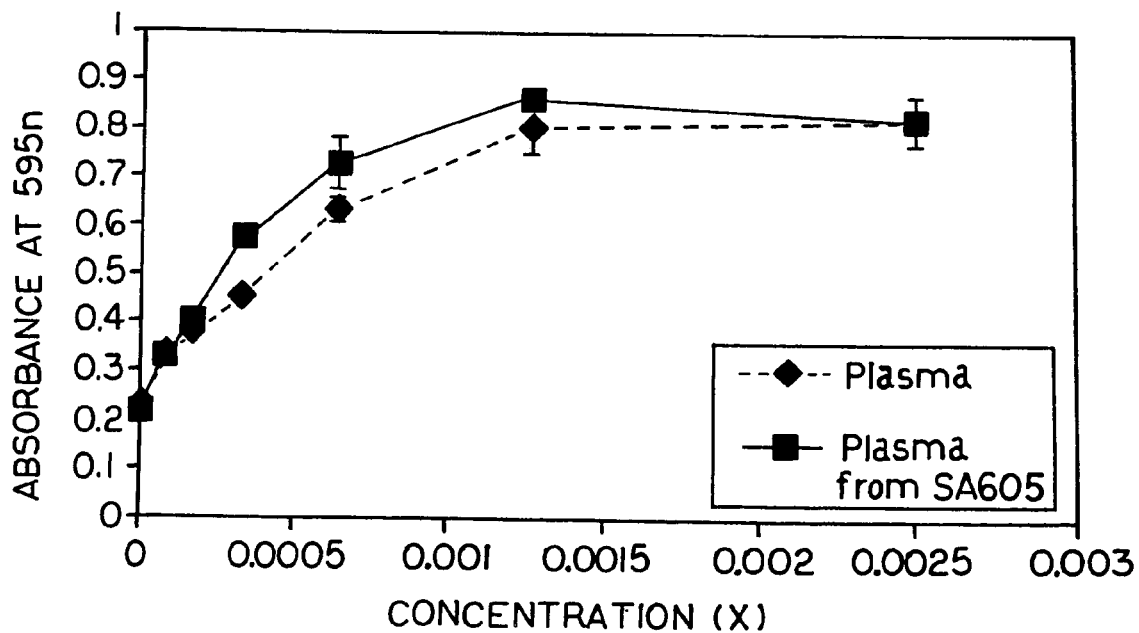
FIG. 4 is a representation of the total protein concentration in plasma alone and in plasma recovered from the polymer packaging material SA60S.

This embodiment demonstrates that recovered aqueous samples from a liquid swollen absorbent gel can be used for detection and analysis of analytes. It also demonstrates that the present method can be used when the exact amount of biological fluid spilled is not known. To illustrate this embodiment, total protein content was measured using light absorbance methods following application of a recovery fluid composed of 330 g/L NaCl solution in distilled water to a liquid swollen absorbent gel. Human blood plasma was isolated from healthy volunteers as described in Example 1. Approximately 1 ml of the plasma was spilled into 100 mg of the absorbent SA60S and left overnight at room temperature. As expected, the polymer rapidly formed a gel within seconds and the gel remained for the duration of the incubation period. An unknown amount of the liquid-filled polymer was then removed using a spatula, weighed using a standard measuring balance and diluted 10 fold in recovery fluid composed of 330 g/L NaCl solution (i.e. concentration of diluted plasma was thus 0.1× of original). Addition of 10-fold excess recovery fluid rapidly disrupted the gel within seconds and the solution became fluid-like. In a parallel experiment, the same lot of human plasma, which was not treated with the packaging polymer SA60S, was also diluted 10 fold in 330 g/L NaCl solution. Subsequently the plasma solutions both in the presence and absence of SA60S were further diluted with standard PBS to obtain concentrations in the range between 0 and 0.002× (FIG. 4). A protein determination kit based on the method of Bradford obtained from Biorad Laboratories (Hercules, Calif.), was used to measure protein concentration in both the SA60S treated and untreated samples. As seen, the level of protein measured in plasma was similar both upon treatment and in the absence of SA60S over the range of dosage studied. This data demonstrates that: i) a recovery fluid as described herein (such as 330 g/L NaCl) is effective at disrupting the gel, ii) the application of recovery fluid does not affect the absorbance measurements, and iii) even if the exact extent of spillage is unknown, the amount of the leaked solution can be accurately estimated using the weighting protocol proposed here.

EXAMPLE 4

Figure 5:
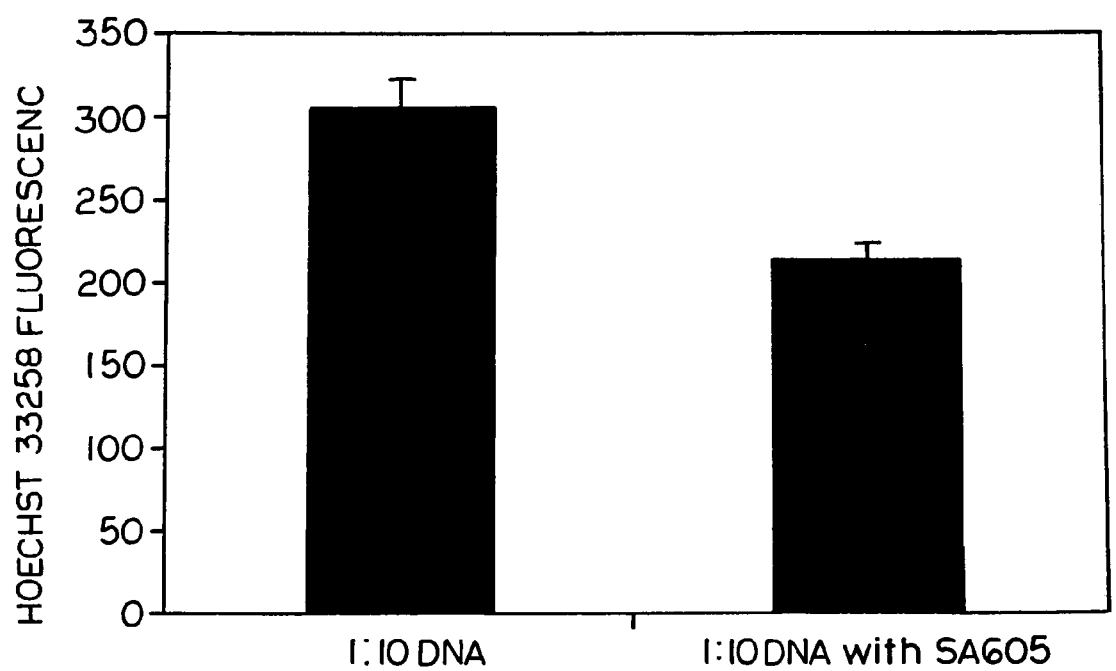
FIG. 5 is a representation of the total mononuclear cell DNA in a sample alone or in a sample containing SA60S packaging material.

This example provides another illustration of the use of this method. Tests were performed to measure the level of DNA (deoxyribonucleic acid) recovered from spilled samples using fluorescence measurement methods. Human mononuclear cells were isolated from healthy volunteers using a density gradient (Mono-Poly from ICN Biomedicals, Costa Mesa, Calif.). The nuclear material was obtained by lysing the cells in three cycles involving rapid cooling of cells for two minutes in liquid nitrogen followed by rapid heating to 37° C. Subsequently, a certain amount of the nuclear lysate was either treated with SA60S or left untreated. After 6 hours of treatment at room temperature, the amount of double stranded DNA was estimated in both samples by diluting the samples by 10 fold in recovery fluid composed of 330 g/L NaCl followed by measurement of fluorescence emitted by Hoechst 33258 dye (Molecular Probes, Inc., OR) bound to the double stranded DNA according to manufacturers instructions. As shown in FIG. 5, the level of DNA measured in recovered sample was within ~30% that of the untreated sample. The slightly lower levels are likely due to some binding of the charged DNA to the polymer and its competition with the DNA binding dye Hoechst 33258. Regardless of this relatively minor effect of the polymer, this experiment illustrates that the method of the present invention may be applied to large polymeric molecules like DNA also. Such applications will be particularly useful during testing for the presence of DNA (or drugs) during forensic investigations.

The foregoing description is for the purpose of illustration and is not to be construed as restrictive. From the teachings of the present invention, those skilled in the art will recognize that modifications may be made without departing from the spirit of the invention.

What is claimed is:

1. A method for recovering an aqueous sample from an absorbent packaging material comprising absorbent fibers, absorbent granules or combinations thereof and wherein the absorbent packaging material has absorbed the aqueous sample and formed a liquid-swollen absorbent gel, comprising the steps of:
   a) contacting the liquid-swollen absorbent gel with a recovery fluid for a sufficient time to disrupt the liquid-swollen absorbent gel and form a recovery mixture, wherein the osmotic pressure of the recovery fluid is higher than the osmotic pressure of the aqueous sample, and
   b) removing the recovery mixture for detection and analysis of desired analytes.

2. The method of claim 1, wherein the osmotic pressure of the recovery fluid is between 1 and 150 atm.

3. The method of claim 2, where the recovery fluid comprises water-soluble molecules having a molecular weight less than 1000 Da.

4. The method of claim 3, wherein the recovery fluid comprises simple carbohydrates.

5. The method of claim 4, wherein the carbohydrates are selected from the group consisting of glucose, fructose and sucrose.

6. The method of claim 3, comprising one or more salts selected from the group consisting of $NH_4NO_3$, $KC_2H_3O_2$, $KNO_2$, KCNS and NaCl.

7. The method of claim 6, wherein the salt is NaCl.

8. The method of claim 1, where the aqueous sample is a biological fluid.

9. The method of claim 8, where the biological fluid is selected from the group consisting of blood, plasma, urine, cerebrospinal fluid, amniotic fluid and lymph.

10. The method in claim 8, wherein the biological fluid further comprises substances selected from the group consisting of toxic or non-toxic chemicals, pharmacological drugs and alcohol.

11. The method in claim 3, wherein the non-biological sample comprises toxic chemicals.

12. The method of claim 1, wherein the aqueous sample is a non-biological fluid.

13. The method in claim 12, wherein the non-biological sample is contaminated water containing agrochemicals or industrial compounds.

14. The method of claim 1, where the absorbent packaging material is a cross-linked polymer.

15. The method of claim 14, where the a cross-linked polymer comprises poly(acrylic acid).

16. The method of claim 15, wherein the cross-linked polymer is ionized with monovalent counter-ions.

17. The method of claim 1, wherein the absorbent fibers are superabsorbent fibers.

18. The method of claim 1, wherein the absorbent granules are superabsorbent granules.

19. A method for recovering an aqueous sample from an absorbent packaging material wherein the absorbent packaging material comprising absorbent fibers, absorbent granules or combinations thereof has absorbed the aqueous sample and formed a liquid swollen absorbent gel, comprising the steps of:
a) estimating the amount of aqueous sample absorbed by the polymer packaging material;
b) contacting the liquid-swollen absorbent gel with recovery fluid for sufficient time to disrupt the liquid swollen absorbent gel and form a recovery mixture, wherein the osmotic pressure of the recovery fluid is greater than the osmotic pressure of the aqueous sample, and wherein the recovery fluid is in excess of the estimated aqueous sample;
c) removing the recovery mixture.

20. The method of claim 19, wherein the volume of the recovery fluid is approximately five times more than the estimated spilled aqueous sample.

21. The method of claim 19, further comprising the step of detecting the presence of an analyte in the recovered sample.

22. The method of claim 19 wherein the absorbent fibers are superabsorbent fibers.

23. The method of claim 19, wherein the absorbent granules are superabsorbent granules.

* * * * *